United States Patent
Randolph et al.

(10) Patent No.: US 6,403,672 B1
(45) Date of Patent: Jun. 11, 2002

(54) PREPARATION AND USE OF PHOTOPOLYMERIZED MICROPARTICLES

(75) Inventors: Theodore Randolph, Niwot; Kristi Anseth; Jennifer L. Owens, both of Boulder; Corinne Lengsfeld, Denver, all of CO (US)

(73) Assignee: University Technology Corporation, Boulder, CO (US)

( * ) Notice: Subject to any disclaimer, the term of this patent is extended or adjusted under 35 U.S.C. 154(b) by 0 days.

(21) Appl. No.: 09/451,481

(22) Filed: Nov. 30, 1999

Related U.S. Application Data

(60) Provisional application No. 60/110,816, filed on Nov. 30, 1998.

(51) Int. Cl.$^7$ .............................. C08F 2/46; C08K 5/04; C08J 3/28
(52) U.S. Cl. ............................ 522/79; 522/80; 522/87; 522/88; 522/89; 522/182; 424/486; 424/489
(58) Field of Search ........................... 522/79, 80, 182, 522/87, 88, 89

(56) References Cited

U.S. PATENT DOCUMENTS

| | | | |
|---|---|---|---|
| 5,496,901 A | * | 3/1996 | DeSimone |
| 5,552,502 A | * | 9/1996 | Odell et al. |
| 5,603,960 A | * | 2/1997 | O'Hagen et al. |
| 5,626,863 A | * | 5/1997 | Hubbell et al. |
| 5,639,441 A | * | 6/1997 | Sievers et al. |
| 5,707,634 A | | 1/1998 | Schmitt ...................... 424/400 |
| 5,770,559 A | * | 6/1998 | Manning et al. |
| 5,814,678 A | * | 9/1998 | Randolph |
| 5,833,891 A | | 11/1998 | Subramaniam et al. ........ 264/7 |
| 5,837,752 A | * | 11/1998 | Shastri et al. |
| 5,874,029 A | * | 2/1999 | Subramaniam et al. |
| 5,902,599 A | * | 5/1999 | Anseth et al. |
| 5,981,474 A | | 11/1999 | Manning et al. ............... 514/2 |
| 6,063,138 A | * | 5/2000 | Hanna et al. |
| 6,143,211 A | * | 11/2000 | Mathiowitz et al. |

FOREIGN PATENT DOCUMENTS

EP 0 464 163 B1 * 4/1995

OTHER PUBLICATIONS

Bodmeier, R. et al. (1995), "Polymeric Microspheres Prepared by Spraying into Compressed Carbon Dioxide," Pharm. Res. 12(8):1211–1217.
Cooper, A.I. and Holmes, A.B. (1998), "Surfactant–Free Synthesis of Cross–Linked Polymer Microspheres," Proc. 5$^{th}$ Meeting of Supercritical Fluids Materials and Natural Products Processing, held Mar. 23–25, 1998, France, pp. 843–848.
Debenedetti, P.G. et al. (1993), "Supercritical Fluids: A New Medium for the Formation of Particles of Biomedical Interest," Proceedings Internatl. Symp. Control Rel. Bioact. Mater. 20, Controlled Release Society, Inc., pp. 141–142.
Debenedetti, P.G. et al. (1993), "Application of supercritical fluids for the production of sustained delivery devices," J. Controlled Release 24:27–44.
Debenedetti, P.G. et al. (1993), "Rapid Expansion of Supercritical Solutions (RESS): Fundamentals and Applications," Fluid Phase Equilibria 82:311–321.
Dixon, D.J. and Johnston, K.P. (1993), "Formation of Microporous Polymer Fibers and Oriented Fibrils by Precipitation with a Compressed Fluid Antisolvent," J. Appl. Polym. Sci. 50:1929–1942.
Langer, R. (1993), "Polymer–Controlled Drug Delivery Systems," Acc. Chem. Res. 26:537–542.
Muggli, D.S. et al. (1998), "Reaction Behavior of Biodegradable, Photo–Cross–Linkable Polyanhydrides," Macromolecules 31:4120–4125.
Oh, J.S. et al. (1999), "Swelling behavior of N–isopropylacrylamide gel particles with degradable crosslinker," Eur. Polym. J. 35(4):621–630 (Abstract Only).
Randolph, T.W. et al. (1993), "Sub–Micrometer–Sized Biodegradable Particles of Poly(L–Lactic Acid) via the Gas Antisolvent Spray Precipitation Process," Biotechnol. Prog. 9:429–435.
Tom, J.W. et al. (1993), "Applications of Supercritical Fluids in the Controlled Release of Drugs," in *Supercritical Fluid Engineering Science*, pp. 238–257.
Tom, J.W. and Debenedetti, P.G. (1991), "Formation of Bioerodible Polymeric Microspheres and Microparticles by Rapid Expansion of Supercritical Solutions," Biotechnol. Prog. 7:403–411.
Yeo, S.–D. et al. (1993), "Formation of Microparticulate Protein Powders Using a Supercritical Fluid Antisolvent," Biotechnol. Bioeng. 41:341–346.

* cited by examiner

Primary Examiner—Susan W. Berman
(74) Attorney, Agent, or Firm—Greenlee, Winner and Sullivan, P.C.

(57) ABSTRACT

Methods of forming polymer particles in situ from polymer precursors such as monomers or oligomers, comprising exposing a composition comprising at least one polymer precursor, a solvent or solvent mixture, and an antisolvent or antisolvent mixture to photoradiation under conditions whereby particles are formed are provided. The polymer precursor may be photosensitive, or a separate polymerization initiator may be used. In a preferred embodiment, the polymer precursor is insoluble in the antisolvent or antisolvent mixture and the solvent or solvent mixture is soluble in the antisolvent or antisolvent mixture at the concentrations used. Polymer particles comprising a polymer and a bioactive material are also provided. The polymer may be erodable, and the polymer particles formed may be used in a variety of applications, including controlled release of bioactive materials such as drugs. Polymer particles formed using the methods of the invention have low residual solvent levels and high additive encapsulation efficiencies. The processes of the invention allow control of particle size and morphology, use low operating temperatures and are useful for efficient bulk production.

44 Claims, 14 Drawing Sheets

PREPARATION AND USE OF PHOTOPOLYMERIZED MICROPARTICLES

CROSS-REFERENCE TO RELATED APPLICATIONS

This application takes priority from U.S. provisional Patent Application No. 60/110,816, filed Nov. 30, 1998, which is hereby incorporated in its entirety by reference to the extent not inconsistent with the disclosure herein.

STATEMENT REGARDING FEDERALLY SPONSORED RESEARCH OR DEVELOPMENT

This invention was made with government support by the National Science Foundation. The federal government may have certain rights in this invention.

BACKGROUND OF THE INVENTION

This invention relates generally to polymer particles and methods of making and using the same.

Small (micron- and nano-sized) polymer particles are useful for many applications, including pharmaceutical uses. Polymer microparticles are useful for injectable and implantable devices because they have a long circulation time in the body and are efficient drug, enzyme, and protein carriers (Tom, J. W. et al. (1993), "Applications of Supercritical Fluids in the Controlled Release of Drugs," in *Supercritical Fluid Engineering Science*, pp. 238–257). Crosslinked polymer microparticles have material property benefits over linear polymer particles including improved mechanical strength, greater control of transport properties, material property adjustability and dimensional stability. Some applications of cross-linked polymers are listed in Cooper, A. L. and Holmes, A. B. (1998) Proceedings of the 5th Meeting of Supercritical Fluids Materials and Natural Products Processing, pp. 843–848. Polymer microparticles (both linear and crosslinked) have been used in applications such as dental composites, biostructural fillers and controlled release devices. Some applications of synthetic bone composites are listed in Popov, V. K. et al. (1998) Proceedings of the 5th Meeting of Supercritical Fluids Materials and Natural Products Processing, pp. 45–50.

Controlled release devices are useful in many applications, from medical to agricultural (Langer, R. (1993), Polymer-Controlled Drug Delivery Systems," Acc. Chem. Res. 26:537–542; U.S. Pat. No. 5,043,280). Controlled release delivery systems for drugs have at a wide variety of advantages over conventional forms of drug administration. Some of these advantages include: decreasing or eliminating the oscillating drug concentrations found with multiple drug administrations; allowing the possibility of localized delivery of the drug to a desired part of the body; preserving the efficacy of fragile drugs; reducing the need for patient follow-up care; increasing patient comfort and improving patient compliance. (Langer, R. (1990), "New Methods of Drug Delivery," Science 249:1527–1533).

Current polymer microparticle manufacturing techniques all suffer from one or more disadvantages. For example, the spray drying technique usually requires evaporation of solvent in hot air. The high temperatures used can degrade sensitive drugs and polymers. In thermal polymerization, monomer is heated to induce polymerization. Again, the high temperatures used can cause degradation (including lowering the activity of biologically active substances).

Emulsion and suspension polymerizations (see, for example, U.S. Pat. No. 5,603,960 (O'Hagan., et al.)) involve combinations of solvents, emulsifiers, and surfactants where dispersed islands of monomer polymerize through chemical reaction in a sea of solvent. These methods often involve operation at high temperatures and thus have the problems discussed above, use large volumes of solutions that are often environmentally unfriendly, and permit only minimal control over particle size and morphology.

A number of different techniques have been developed to form small particles of polymers using the solvent power of supercritical fluids. Supercritical fluids have liquid-like densities, very large compressibilities, viscosities between those of liquids and gases, and diffusion coefficients that are higher than liquids. Due to the high compressibility, the density (and solvent power) of a supercritical fluid can be adjusted between gas- and liquid-like extremes with moderate changes in pressure (Debenedetti, P. G. et al. (1993), "Rapid Expansion of Supercritical Solutions (RESS): Fundamentals and Applications," Fluid Phase Equilibria 82:311–321).

The Rapid Expansion of Supercritical Solution (RESS) technique has been used to form small particles of poly(L-lactic acid) (Debenedetti, P. G. et al. (1993), "Supercritical Fluids: A New Medium for the Formation of Particles of Biomedical Interest," Proceed. Interm. Symp. Control Rel. Bioact. Mater. 20:141–142) and particles of poly(DL-lactic acid) with embedded lovastatin (Tom, J. W. et al. (1993), "Applications of Supercritical Fluids in the Controlled Release of Drugs," in *Supercritical Fluid Engineering Science*, pp. 238–257). In the RESS technique, particles of polymer may be made when a polymer is dissolved in a supercritical fluid (usually carbon dioxide) followed by rapid expansion of the fluid. This technique is limited in applicability to compounds that are soluble in the supercrifical fluid. Since most drugs are not soluble in supercritical fluids and most polymers have very low solubility in supercritical fluids, the RESS process is not broadly applicable for drug encapsulation (McHugh, M. and Krukonis, V. (1994) *Supercritical Fluid Extraction*, Butterworth-Heinemann).

In the Precipitation by a Compressed Antisolvent (PCA) technique (also known as the Gas Antisolvent technique), a solid of interest is dissolved in a solvent and the resulting solution is sprayed into a compressed antisolvent (see, for example, U.S. Pat. Nos. 5,833,891 and 5,874,029). In this technique, the antisolvent and solvent are soluble, but the solid of interest is not soluble in the antisolvent. The antisolvent is believed to extract the solvent, precipitating particles of the solid of interest (Randolph, T. W. et al. (1993)Biotech. Prog. 9:429–435). Microparticles of insulin have reportedly been formed using this technique (Yeo, S.-D. et al. (1993), "Formation of Microparticulate Protein Powders Using a Supercritical Fluid Antisolvent," Biotech. Bioeng. 41:341–346) and polymer microparticles have been formed using polymer starting materials (Bodmeier, R. et al. (1995), "Polymeric Microspheres Prepared by Spraying into Compressed Carbon Dioxide," Pharm. Res. 12(8) :1211–1217; U.S. Pat. Nos. 5,833,891; 5,874,029).

There is a need for polymer particles with low residual solvent levels, high additive encapsulation efficiencies, and processes of making polymer particles that allow control of particle size and morphology, with low operating temperatures and efficient bulk production capability. Formation of polymer particles with erodable surfaces are also needed for controlled release of drugs, for example. In particular, highly crosslinked polymer networks with erodable surfaces are desired. In addition, there is a need for a process that produces polymer particles in situ from polymer precursors such as monomers or oligomers.

BRIEF SUMMARY OF THE INVENTION

In a general description of the invention, a method of forming polymer particles comprising exposing a composition comprising at least one polymer precursor, a solvent or solvent mixture, and an antisolvent or antisolvent mixture to photoradiation under conditions whereby particles are formed is provided. If the precursor is not photosensitive, at least one photoinitiator is present in the composition. The solvent is not required if the polymer Sri precursor is liquid or liquifiable. If used, the solvent is chosen so that the polymer precursor is soluble in the solvent at the concentrations used, and the antisolvent and solvent are soluble in each other at the concentrations used. The polymer precursor is preferably insoluble in the antisolvent, but as long as nucleation and particle formation occur, any solubility condition may be present. Bioactive materials such as drugs may also be included in the composition.

Also provided is a method of forming polymer particles comprising contacting a solution comprising a solvent or solvent mixture and at least one polymer precursor with an antisolvent or antisolvent mixture under conditions whereby particles are generated; and exposing said particles to photoradiation, whereby polymer particles are formed. Preferably the polymer precursor is insoluble in the antisolvent or antisolvent mixture.

Also provided are polymer particles prepared by the methods of the invention that are between about 0.001 $\mu$m to about 100 $\mu$m in diameter. Linear and crosslinked polymer particles may be formed using the methods of the invention.

Also provided is a method of forming polymer particles comprising: substantially dissolving at least one polymer precursor in a solvent or solvent mixture to form a solution; contacting said solution with an antisolvent or antisolvent mixture in which said polymer precursor is insoluble to form a composition comprising said precursor, and a substantially soluble mixture of said solvent or solvent mixture and said antisolvent or antisolvent mixture; and exposing said composition to sufficient photoradiation to initiate polymerization whereby polymer particles are formed.

Also provided is a method of forming polymer particles comprising: establishing a flow of antisolvent in an optically accessible chamber; contacting a solution comprising at least one polymer precursor and at least one polymerization initiator dissolved in a solvent or solvent mixture with said antisolvent under conditions whereby particles are formed; and exposing said particles to photoradiation whereby polymer particles are formed.

Also provided is a method of forming copolymers comprising: dissolving or suspending at least two polymer precursors or at least one polymer precursor and at least one polymer in a solvent or solvent mixture to form a solution; contacting said solution with an antisolvent or antisolvent mixture to form a composition comprising: said precursors or said precursor and polymer; a soluble mixture of said solvent or solvent mixture and said antisolvent or antisolvent mixture; and exposing said composition to photoradiation whereby copolymer particles are formed.

Copolymers may also be formed where at least one polymer precursor or at least one polymer are present in a solvent or solvent mixture, and at least one polymer precursor or at least one polymer are present in the antisolvent or antisolvent mixture, providing that at least one polymer precursor is present.

Also provided is a method of forming particles comprising a bioactive material and a polymer comprising: exposing a composition comprising at least one bioactive material, at least one polymer precursor and an antisolvent or antisolvent mixture to photoradiation under conditions whereby particles are formed.

Polymers formed may be erodable or nonerodable, biodegradable or nonbiodegradable and biocompatible or non-biocompatible. Polymer particles formed using the methods of the invention may be used for controlled release of a desired substance in an organism or system. Provided is a method of controlled release of a desired substance comprising: preparing polymer particles that comprise a degradable polymer and a desired substance; and exposing said polymer particles to conditions under which the polymer is degraded.

Methods of forming degradable particles comprising a degradable polymer and a pharmaceutical product comprising: exposing a composition comprising a solvent or solvent mixture, at least one polymer precursor capable of forming a degradable polymer, at least one pharmaceutical product, and an antisolvent or antisolvent mixture to photoradiation whereby polymer particles that contain a degradable polymer and a pharmaceutical product are formed are provided.

A pharmaceutical composition comprising polymer particles produced by the methods of the invention and a pharmaceutically acceptable carrier are also provided. Polymer particles comprising at least one bioactive material and at least one polymer are also provided.

Crosslinked polymer particles comprising a degradable polymer are also provided. Crosslinked polymer particles comprising a polyanhydride are provided. Biodegradable crosslinked polymer particles are also provided. Crosslinked polymer particles further comprising at least one bioactive material are also provided.

An apparatus is provided for producing polymer microparticles which comprises: a reaction chamber; at least one inlet into said reaction chamber through which an antisolvent or antisolvent mixture, at least one polymer precursor insoluble in said antisolvent or antisolvent mixture, and a solvent or solvent mixture soluble in said antisolvent or antisolvent mixture pass into said chamber; and a light source optically connected to said chamber wherein during operation of the chamber said polymer precursor is polymerized. The apparatus may be used with a photosensitive polymer precursor, or a polymerization initiator may be added.

Advantages of this photopolymerization technique include morphological control through polymerization rate, process conditions, and initiation location. Processing time remains short while processing temperatures remain low. Low operating temperatures are important since many potential encapsulation additives degrade at moderate temperatures. In addition, particles formed using the method of the invention do not require further processing, for example solvent removal, before use.

Further objects and advantages of this invention will be apparent from a consideration of the drawings and description herein.

"Microparticles" as used herein means particles that are less than about 100 $\mu$m in diameter. "Nanoparticles" are particles that are less than about 1 $\mu$m in diameter. Both microparticles, nanoparticles and particles of other sizes may be produced by the methods of the invention by changing process parameters and choice of materials. Methods of changing the process parameters and materials are described herein, or determinable by one of ordinary skill in the art without undue experimentation.

"Polymer precursor" means a molecule or portion thereof which can be polymerized to form a polymer or copolymer. Polymer precursors include any substance that contains an unsaturated moiety or other functionality that can be used in chain polymerization, or other moiety that may be polymerized in other ways. Such precursors include monomers and oligomers. Preferred precursors include those that are capable of being polymerized by photoradiation. One class of polymer precursors of the invention are those that are insoluble in the antisolvent or antisolvent mixture. Another class of polymer precursors of this invention are photosensitive. If a polymer precursor that polymerizes photochemically is used (photosensitive polymer precursor), a separate photoinitiator does not need to be used. Examples of photosensitive polymer precursors include tetramercaptopropionate and 3,6,9,12-tetraoxatetradeca-1,13-diene. Another class of precursors that may be used are radically polymerizable precursors. Another class of precursors that may be used are ionically polymerizable precursors. Another class of precursors that are useful in the invention are cationic precursors.

Some examples of precursors that are useful in the invention include ethylene oxides (for example, PEO), ethylene glycols (for example, PEG), vinyl alcohols (for example, PVA), vinyl pyrrolidones (for example, PVP), ethyloxazolines (for example, PEOX), amino acids, saccharides, proteins, anhydrides, vinyl ethers, amides, carbonates, phenylene oxides (for example, PPO), acetals, sulfones, phenylene sulfides (for example, PPS), esters, fluoropolymers, imides, amide-imides, etherimides, ionomers, aryletherketones, olefins, styrenes, vinyl chlorides, ethylenes, acrylates, methacrylates, amines, phenols, acids, nitriles, acrylamides, maleates, benzenes, epoxies, cinnamates, azoles, silanes, chlorides, epoxides, lactones and amides.

As used herein, "polymer" includes copolymers. "Copolymers" are polymers formed of more than one polymer precursor. Polymers that can be formed using the methods of this invention include those which are prepared from precursors that, in a preferred embodiment are soluble in a solvent that is soluble in an antisolvent and can be polymerized with light initiation. One class of polymers that may be prepared using the method of this invention include those that are degradable, preferably biodegradable. Another class of polymers that may be prepared using the method of this invention include those that are not degradable. Another class of polymers that may be prepared using the method of this invention include those that comprise one or more degradable polymers and one or more nondegradable polymers. Another class of polymers that may be prepared using the method of this invention include poly lactic acids. In a preferred embodiment of the invention, the polymers are degradable or erodable.

"Degradable or erodable polymers" are those that degrade upon exposure to some stimulus, including time. Degradable or erodable polymers include biodegradable polymers. Biodegradable polymers degrade in a biological system, or under conditions present in a biological system. Preferred biodegradable polymers degrade in an organism, preferably a mammal, and most preferably human. Examples of biodegradable polymers include those having at least some repeating units representative of at least one of the following: an alpha-hydroxycarboxylic acid, a cyclic diester of an alpha-hydroxycarboxylic acid, a dioxanone, a lactone, a cyclic carbonate, a cyclic oxalate, an epoxide, a glycol, and anhydrides. Preferred degradable or erodable polymers comprise at least some repeating units representative of polymerizing at least one of lactic acid, glycolic acid, lactide, glycolide, ethylene oxide and ethylene glycol.

A class of polymers included in this invention are biocompatible polymers. One type of biocompatible polymers degrade to nontoxic products. Specific examples of biocompatible polymers that degrade to nontoxic products that do not need removal from biological systems include poly (hydro acids), poly (L-lactic acid), poly (D,L-lactic acid), poly (glycolic acid) and copolymers thereof. Polyanhydrides have a history of biocompatibility and surface degradation characteristics (Langer, R. (1993) Acc. Chem. Res. 26:537–542; Brem, H. et al. (1995) Lancet 345:1008–1012; Tamada, J. and Langer, R. J. (1992) J. Biomat Sci.-Polym. Ed. 3:315–353).

Another class of polymers that may be prepared using the method of this invention include particles that are a suitable size for injection or administration orally or incorporated in a preparation suitable for oral administration. For oral or injectable delivery, it is preferred that most particles are less than 50 microns in diameter. Another class of particles that may be prepared using the method of this invention include those that are a suitable size for inhalation or pulmonary delivery. For pulmonary delivery, it is preferred that greater than about 90 weight percent of all solid particles in an administered pharmaceutical formulation are of a size smaller than about 10 microns and more preferably at least about 90 weight percent are smaller than about 6 microns, and even more preferably at least about 90 percent of all solid particles are from about 1 micron to about 6 microns. Particularly preferred for pulmonary delivery applications are particles of from about 2 microns to about 5 microns in size. Other classes of particles of suitable size for various applications are included in the methods of the invention.

Solvents useful in the invention include those that dissolve some portion of a polymer precursor and are preferably at least partially soluble in the antisolvent used. Preferably the solvent is miscible in the antisolvent or antisolvent mixture at the temperature and pressure of operation. Preferred solvents are not water. Some examples of preferred solvents include methylene chloride, methanol, toluene, propanol, ethanol, acetone, ethers, hexanes and heptane. If a liquid or liquidizable polymer precursor is used, a solvent is not necessary. One solvent or a mixture of solvents may be used.

Photoinitiators that are useful in the invention include those that can be activated with light and initiate polymerization of the polymer precursor. Preferred initiators include azobisisobutyronitrile, peroxides, phenones, ethers, quinones, acids, formates. Cationic initiators are also useful in the invention. Preferred cationic initiators include aryldiazonium, diaryliodonium, and triarylsulfonium salts. Most preferred initiators include Rose Bengal (Aldrich), DAROCUR 2959 (2-hydroxy-1-[4-(hydroxyethoxy) phenyl]-2-methyl-1-propanone, D2959, Ciba-Geigy), IRGACURE 651 (2,2dimethoxy-2-phenylacetophenone, 1651, DMPA, Ciba-Geigy), IRGACURE 184 (1-hydroxycyclohexyl phenyl ketone, 1184, Ciba-Geigy), IRGACURE 907 (2-methyl-1-[4-(methylthio)phenyl]-2-(4-morpholinyl)-1-propanone, 1907, Ciba-Geigy), camphorquinone (CQ, Aldrich), isopropyl thioxanthone (QUANTACURE ITX, Great Lakes Fine Chemicals LTD., Cheshire, England). CQ is typically used in conjunction with an amine such as ethyl 4-N,N-dimethylaminobenzoate (4EDMAB, Aldrich) or triethanolamine (TEA, Aldrich) to initiate polymerization.

The wavelengths and power of light useful to initiate polymerization depends on the initiator used or the wavelength (or wavelengths) will activate the photosensitive precursor. A combination of photosensitive precursor(s) and photoinitiator(s) may be used. When Rose Bengal is used as the initiator, a visible light source is preferably used. Light used in the invention includes any wavelength and power capable of initiating polymerization. Preferred wavelengths of light include ultraviolet or visible. Any suitable source may be used, including laser sources. The source may be broadband or narrowband, or a combination.

Chamber windows made from various materials may be used in the method of this invention. In addition, a filter may used to block a wavelength from reaching the chamber, or allow a selected wavelength or wavelengths of light to reach the chamber. The chamber windows themselves may act as this filter, or a separate filter or filters may be used in conjunction with the chamber windows.

In one embodiment, a broadband light source may be used, and by selecting chamber window compositions and/or filter combinations, the selected wavelength or wavelengths of light may pass through the chamber. Light of different selected wavelengths may pass through the same chamber at various locations. This feature may be used to activate more than one photoinitiator.

As used herein, "antisolvent" is a substance in which the polymer precursor is substantially not soluble. It should be understood that it is possible that the antisolvent may be capable of dissolving some amount of the precursor without departing from the scope of the present invention. The antisolvent is, however, preferably incapable of dissolving a significant portion of the precursor such that at least a significant portion of precursor is, in effect, not soluble in the antisolvent. Preferably, the antisolvent precipitation is conducted under thermodynamic conditions which are near critical or supercritical relative to the antisolvent fluid. The antisolvent preferably comprises any suitable fluid for near critical or supercritical processing. These fluids include carbon dioxide, ammonia, nitrous oxide, methane, ethane, ethylene, propane, butane, pentane, benzene, methanol, ethanol, isopropanol, isobutanol, fluorocarbons (including chlorotrifluoromethane, monofluoromethane, hexafluoroethane and 1,1-difluoroethylene), toluene, pyridine, cyclohexane, m-cresol, decalin, cyclohexanol, o-xylene, tetralin, aniline, acetylene, chlorotrifluorosilane, xenon, sulfur hexafluoride, propane and others. Carbon dioxide, ethane and propane are preferred antisolvents. Most preferably, carbon dioxide is used as the antisolvent. One antisolvent, or a mixture of different antisolvents may be used.

As used herein, "supercritical or near supercritical fluid" means a substance that is above its critical pressure and temperature or is substantially near its critical pressure and temperature.

Components that are "contacted" with each other refers to two or more components physically near each other. Components that are contacted with each other are preferably in intimate contact with each other so that they may react with each other or affect each other.

A "bioactive" material is any substance which may be administered to any biological system, such as an organism, preferably a human or animal host, and causes some biological reaction. Bioactive materials include pharmaceutical substances, where the substance is administered normally for a curative or therapeutic purpose. The bioactive material may comprise a protein or other polypeptide, an analgesic or another material.

A "polymer shell" may be a continuous coating of polymer over some substance, but the coating is not required to be continuous. The polymer shell may have nonhomogeneous I, regions where there is no coating, or regions where the coating is thicker than in other areas. The polymer shell may be composed of different materials. Preferably, the polymer shell is a homogeneous coating with uniform thickness. "Encapsulated" is intended to indicate a substance, such as a bioactive material, is homogeneously distributed throughout the polymer.

"Linear polymers" are those polymers that are composed of individual polymer chains that do not have bonds connecting the chains. "Crosslinked polymers" are those polymers that have bonds between polymer chains. Branched polymers are also included in the invention.

"Soluble" does not necessarily mean completely soluble. As long as some portion of one substance dissolves in another substance, the substances are soluble in each other. Likewise, "insoluble" does not necessarily mean that no amount of one substance will dissolve in another substance.

A "composition" of substances is not intended to mean the substances are soluble or miscible with each other, or react with each other. A "composition" is merely intended to mean all listed substances are present.

DETAILED DESCRIPTION OF THE INVENTION

Figure 1:
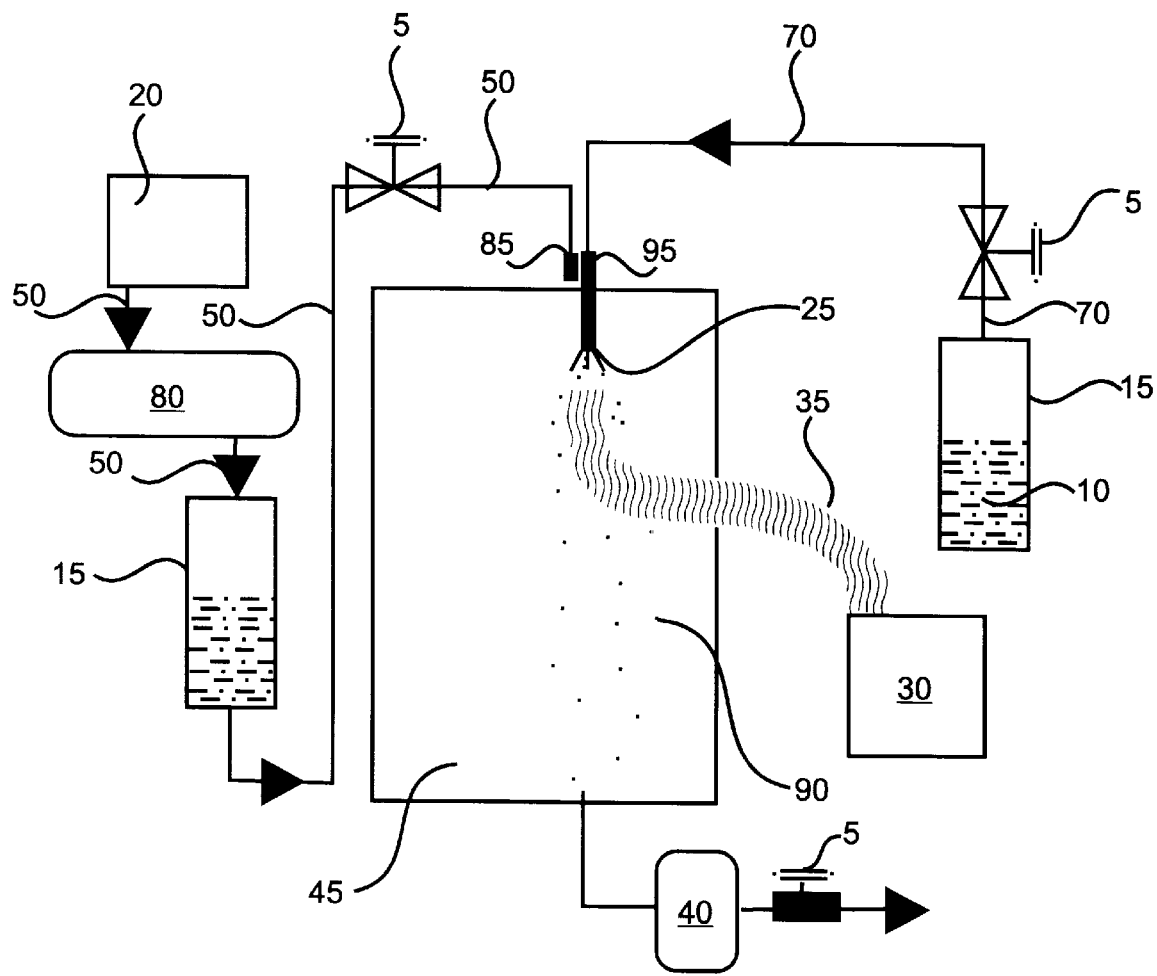
FIG. 1 is a schematic diagram of a photopolymerization system.

A process for photopolymerizing polymer particles in-situ with antisolvent precipitation is provided. Photopolymerization occurs when solutions of polymer precursor and solvent are exposed to light of sufficient power and of a wavelength capable of initiating polymerization while being contacted with an antisolvent at reduced temperature ($T_A$) and it pressure ($P_A$). The polymerization may be initiated by a polymerization initiator activated by light, or a photosensitive polymer precursor may be used. If a photosensitive polymer precursor is used, a separate photoinitiator is optional. The polymer precursor and solvent solution may be homogeneous, but that is not required. This type of polymerization results in particles with a wide range of morphologies, sizes and physical characteristics adjustable by changing the process conditions. The polymer particles produced by the methods of the invention do not require any further processing (for example solvent removal) before they may be used.

Not wishing to be bound by theory, it is believed that the chamber conditions coupled with the antisolvent properties (high diffusivity, low viscosity, and high solvating capacity) facilitates the extraction of the solvent from the solution leaving mostly precursor and initiator (if used). At the same time, these precursor/initiator particles receive photons from the UV source, initiating the polymerization.

The reduced temperature is the ratio of the operating temperature over the critical temperature for the antisolvent.

$$T_r = \frac{T_{operating}}{T_{critical}}$$

The reduced pressure is the ratio of the operating pressure over the critical pressure for the antisolvent.

$$P_r = \frac{P_{operating}}{P_{critical}}$$

In the methods of the invention, $T_A$=0.7 to 1.3, preferably $T_A$=0.9 to 1.1. In the methods of the invention, $P_A$=0.5 to 2, preferably, $P_A$=0.75 to 1.5.

The precursor/initiator/solvent should remain at a temperature such that the initiators (if used), precursors and any desired additives are not degraded to an extent that is unacceptable for the particular application. The methods of this invention may be used where the antisolvent is not at reduced pressure and temperature to produce polymer particles, as long as particle formation and nucleation occur. The methods of the invention may also be used to produce polymer particles when the solvent or solvent system used is not completely miscible in the antisolvent or antisolvent mixture, or when the precursor is soluble to some extent in the antisolvent or antisolvent mixture.

Polymers with many different morphologies and physical properties may be produced using the methods of this invention. The morphology changes in polymers formed by changing conditions in the PLA experiment have been studied (Dixon, D. J. and Johnston, K. P. (1993), "Formation of Microporous Polymer Fibers and Oriented Fibrils by Precipitation with a Compressed Fluid Antisolvent," J. Appl. Polym. Sci. 50:1929–1942).

Polymers with improved mechanical strength, polymer-encapsulated bioactive materials where the biomaterial has controlled transport properties through the polymer, and polymers that are capable of degrading or remaining substantially intact in a given system, for example an organism such as a human or other mammal, may be prepared using the methods of this invention. Nondegradable polymers may be formed using the methods of this invention. Polymer particles may be formed using the methods of the invention for use in many applications such as agricultural controlled release of fertilizer, use as fillers, and other applications. In addition to polymer particles, polymer fibers and porous polymer particles, for example, are achievable by changing one or more process parameters such as the solvent flow rate, polymer precursor type and functionality, photoinitiator concentration, initiation rate, chamber operating temperature or pressure, among other parameters.

For example, increasing the concentration of polymer precursor in the solution increases the diameter of the polymer particles formed. In addition, initiating polymerization some distance after the particles have been formed increases the diameter of the polymer particles formed. The diameter of the polymer particles formed can be increased by manipulating the nozzle size, increasing the concentration of monomer, increasing the temperature. Polymer fibers as opposed to more circular particles can be formed by using slower flow rates of the precursor/initiator/solvent.

Copolymers may also be made using this method, as well as bioerodable polymer particles which can be used, for example, in controlled release applications. Polymers with rat m crosslinked polymer networks may also be formed using the methods of this invention. The extent of crosslinking may be controlled by, for example, controlling the carbon-carbon double bond concentration and time of exposure to the initiating stimulus.

Additives of various sorts may be added to the precursor/initiator/solvent solution or the antisolvent. These additives may include, but are not limited to: plasticizers, coloring agents, encapsulation agents, bioactive materials such as drugs of various kinds, and other inert or bioactive particles.

The degradability of these materials can further be controlled by varying polymer composition and morphology. This permits tuning degradation devices to match a desired release rate or release profile. Homogeneous encapsulation of a drug, for example, into polymer particles in a single manufacturing step is possible using the methods of this invention. Changing the size and morphology of the degradable particles allows control over the dose and duration of the drug delivery.

A variety of embodiments of the invention are possible. For example, one drug may be encapsulated in a polymer particle using the methods of the invention. Then, a second polymer precursor, initiator and drug may be used to encapsulate a second drug over the first particle. This will result in a particle that has two or more different bioactive materials with different release profiles. This is useful in a variety of different therapeutic applications.

Methods of determining appropriate dosages for bioactive materials are well known to one of ordinary skill in the art. Polymer particles and compositions comprising bioactive materials are administered by methods well known in the art, or by adapting methods well known in the art.

This invention is useful for other controlled release of materials other than drugs. Other applications include controlled release of fragrances and pesticides. Particles may be made using the methods of the invention that release corrosion inhibitors over a specified time. This may be useful in pipeline applications. Other uses are readily apparent to one of ordinary skill in the art without undue experimentation.

To circumvent potential problems associated with solubilizing a drug in an organic solvent such as microphase separation and consequent burst effects, the photopolymerization technique described herein can be combined with a solubilization technique known as hydrophobic ion-paring (HIP) to form homogeneous solutions of drug, monomer and initiator in an organic solvent and photopolymerized drug-encapsulated microparticles. HIP is described in U.S. Pat. Nos. 5,981,474 and 5,771,559, hereby incorporated by reference to the extent not inconsistent with the disclosure herein. HIP is a technique whereby ionic pharmaceutical agents can be directly solubilized in organic solvents. HIP consists of pairing charges on the molecule with oppositely charged, hydrophobic organic ions, effectively increasing the molecule's solubility in low-dielectric organic solvents. The photopolymerization method described herein may be used in combination with HIP to encapsulate a therapeutic agent in polymer particles.

Apparatus for Polymerization Experiments FIG. 1 illustrates an apparatus of this invention for providing polymer particles. The apparatus has a chamber (45) with one or more inlets (85, 95) that allow substances to pass into chamber (45). In a particular embodiment antisolvent (20) is connected to optional oxygen scrubber (80) through connecting tubing (50). Oxygen scrubber (80) is connected to pump (15) through connecting tubing (50). Pump (15) is connected to valve (5) with connecting tubing (50). Valve (5) is connected to inlet (85) through connecting tubing (50). Inlet (85) allows antisolvent (20) to enter chamber (45). Pump (15) is used to pump solution (10) comprising one or more polymer precursors, one or more initiators and one or more solvents to valve (5) through connecting tubing (70). Solution (10) is pumped to inlet (95) through connecting tubing (70). Inlet (95) allows solution (10) to enter injector (25) inside chamber (45). Light pipe (35) passes light from light source (30) into chamber (45). After polymer particle formation, particles (90) pass out of chamber (45) to filter (40) and valve (5).

The embodiment described by FIG. 1 illustrates more than one inlet (85 and 95). In an alternative embodiment, the antisolvent and solution pass into the chamber through one inlet. The precursor/initiator/solvent may also be sprayed into a stream of antisolvent or antisolvent mixture. In another alternative embodiment, there are multiple inlets for various components.

In operation, the following preferred procedure is used. Antisolvent (20) is optionally deoxygenated with oxygen scrubber (80). Antisolvent (20) is pumped with one or more pumps (15) through connecting tubing (50) to valve (5). Antisolvent (20) is then pumped into optically accessible high pressure chamber (45) through inlet (85). The flow rate of antisolvent (20) into chamber (45) is typically about 25 ml/min. An optional heating or cooling source (not shown) may be positioned in any suitable location to provide any necessary heating or cooling to the antisolvent, the chamber, or any part of the apparatus or any component thereof Antisolvent (20) is preferably pressurized and heated so that it is at or above its critical pressure and critical temperature. Chamber (45) is allowed to equilibrate at the desired temperature and pressure (preferably at or above the critical temperature and pressure of the antisolvent). At least one polymer precursor and at least one photoinitiator are dissolved or suspended in a suitable solvent to form solution (10). Solution (10) is pressurized to the desired pressure with pump (15). Solution (10) is pumped through connecting tubing (70) to valve (5) and pumped through connecting tubing (70) to inlet (95). Solution (10) passes through inlet (95) into injector (25) into chamber (45). In one embodiment, injector (25) is a stainless steel tube with a 100 $\mu$m opening which injects solution (10) into chamber (45). In another embodiment, injector (25) is any type of injector known in the art, including ultrasonic nozzles and laser drilled holes. Many different nozzles may be used, including a stainless steel capillary tube, a quartz capillary tube, a sonicated nozzle, and a converging diverging nozzle with a premixing chamber. The injector and inlet are not required to be separate components. The flow rate of solution (10) through injector (25) is typically about 0.1 to about 1 ml/min. Light source (30) provides the necessary photons to initiate photopolymerization at a desired distance (in one embodiment, 2–3 cm) below solution injector (25). In one embodiment, light source (30) is a ultraviolet or visible light source at about 800 to about 6300 mW/cm$^2$ (30). The light is transferred from light source (30) into chamber (45) using any suitable means, including optical fiber (35). Particles (90) may be collected by any suitable means, including the use of filter (40). A 0.2 $\mu$m filter is used in one embodiment, but any suitable pore size may be used. The size of the pores of the filter needed will depend on the size of the particles formed and the desired size of particles collected. Particles may be transferred from filter (40) through valve (5).

The chamber itself in a preferred embodiment is a 5"×4"×9" long stainless steel chamber with a volume of 100 ml. Tempered borosilicate windows (3.5" long each) are used. The chamber weighs about 50 pounds. Other embodiments of the chamber may be used.

Alternate Apparatus for Continuous Processing

Figure 2:
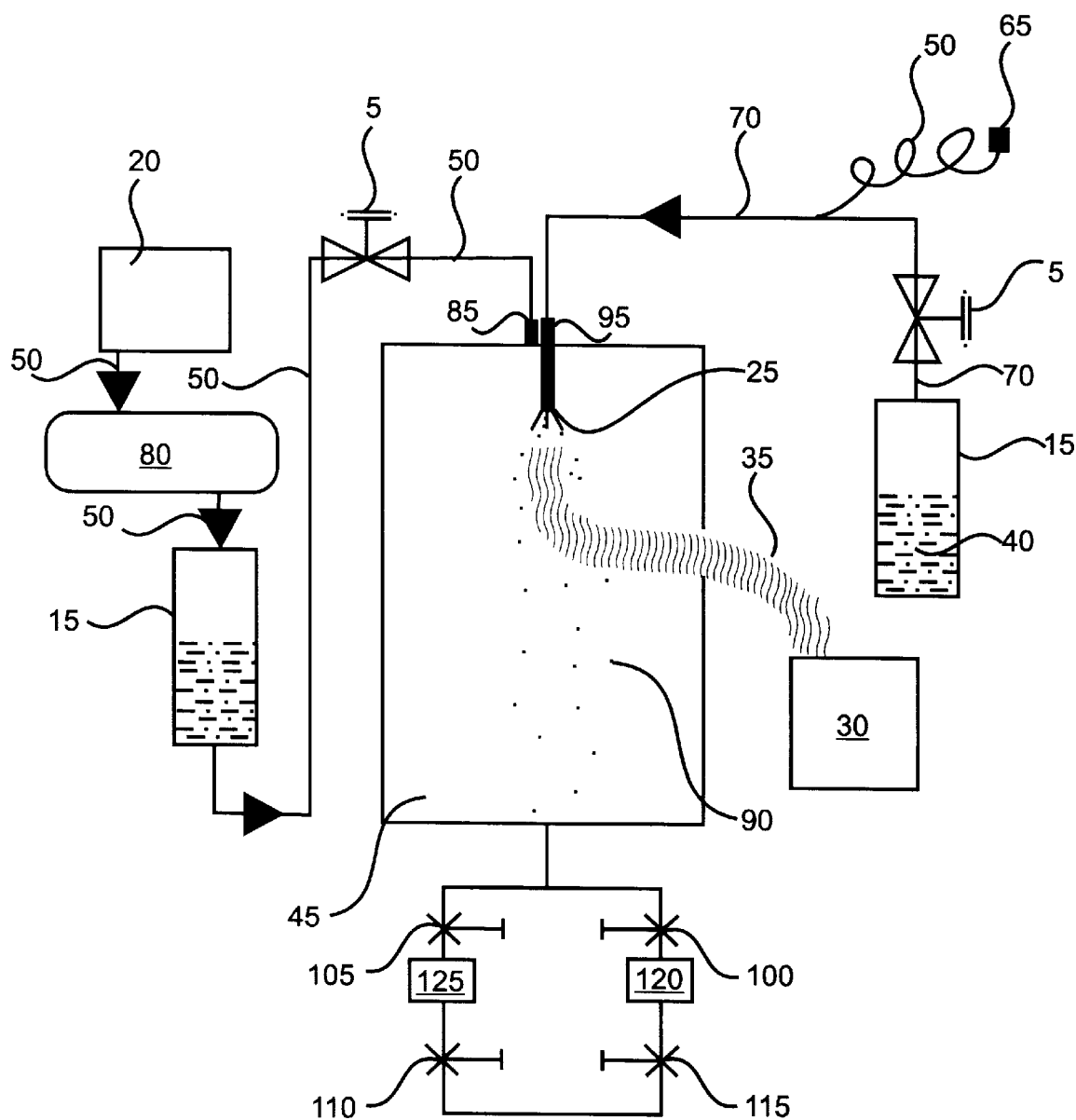
FIG. 2 is a schematic diagram of a continuous photopolymerization system.

Alternatively, the apparatus may be operated in a continuous mode. This is shown in FIG. 2. In this embodiment, injector loop (60) with injection port (65) such as those used in an HPLC apparatus may be added to the apparatus to allow processing of multiple solutions or multiple samples of the same solution without the time consuming pressurizing and depressurizing cycles that would otherwise be required. In this embodiment, a flow of solvent (40) is maintained through connecting tubing (70) and a solution of polymer precursor/initiator and solvent is injected into the solvent flow through injection port (65).

A series of valves and filters may be used to enable particle collection without depressurizing the system. This is also shown in FIG. 2. The flow path exiting the chamber is split. Particles maybe collected on filter (125) by closing valve (100) and opening valve (105). By closing valve (105) and opening valve (100), particles may be collected on filter (120). While particles are being collected on filter (120), filter (125) may be replaced. This way particles may be collected continuously by routing the flow. This allows a continuous, not batch, process to be maintained, and greater amounts of polymer particles may be produced.

The apparatuses described above are only some of the possible apparatuses that may be used to carry out the invention. Other embodiments of the apparatus or components of the apparatus will be readily apparent to those of ordinary skill in the art. For example, the solution of polymer precursor(s) and photoinitiator(s) may pass into the chamber through other diameter injectors or injector types other than those mentioned specifically. The solution of polymer precursor(s) and photoinitiator(s) may be optionally heated or cooled in any suitable location. Any suitable light source may be used, and any suitable method of bringing light to the chamber may be used. The light is brought into the chamber at any desired location. The range of possible modifications is well known to one of ordinary skill in the art without undue experimentation.

The invention will be further understood by reference to the following examples intended as illustrations, not limitations.

EXAMPLES

Preparation of Methacrylated Sebacic Anhydride

The monomer, methacrylated sebacic anhydride (MSA), was prepared by combining 40 g sebacic acid (Aldrich) with 88 ml methacrylic anhydride (Aldrich) and refluxing for approximately 1 hour. This process, shown in Scheme 1, converts the dicarboxylic acid to the anhydride monomer which is subsequently dissolved in dry methylene chloride (Fisher) and precipitated in petroleum ether (Aldrich) for purification and recovery (U.S. Pat. No. 4,789,724).

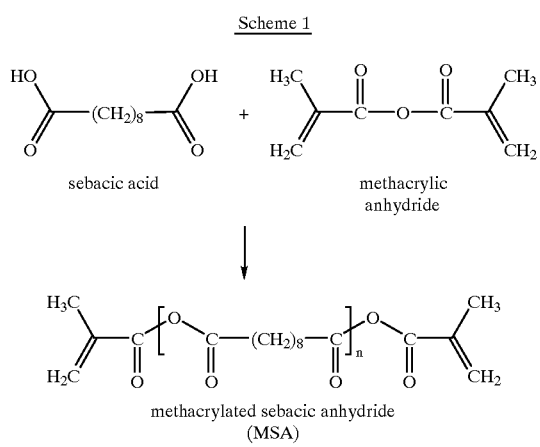

Scheme 1

Proton NMR spectroscopy (Varian VXR-300S) was used to verify the existence of the characteristic methacrylate end-capped =$CH_2$ protons that give peaks at 5.8 and 6.2 ppm. infrared spectroscopy (IR) shows the presence of the methacrylate double bond group at 1635 and confirmed the conversion of the acid groups to the anhydride (Muggli, D. S. et al. (1998) Macromolecules 31:4120–4125). After forming the dimethacrylated monomeric anhydride, the monomer can be oligomerized through a condensation polymerization under vacuum at a temperature of 60° C. A ratio of the integrated area of the =$CH_2$ proton peaks to the internal protons in the MSA backbone from the NMR analysis suggests a number average degree of oligomerization of ~6 repeat units.

Initiator Selection

Figure 3:
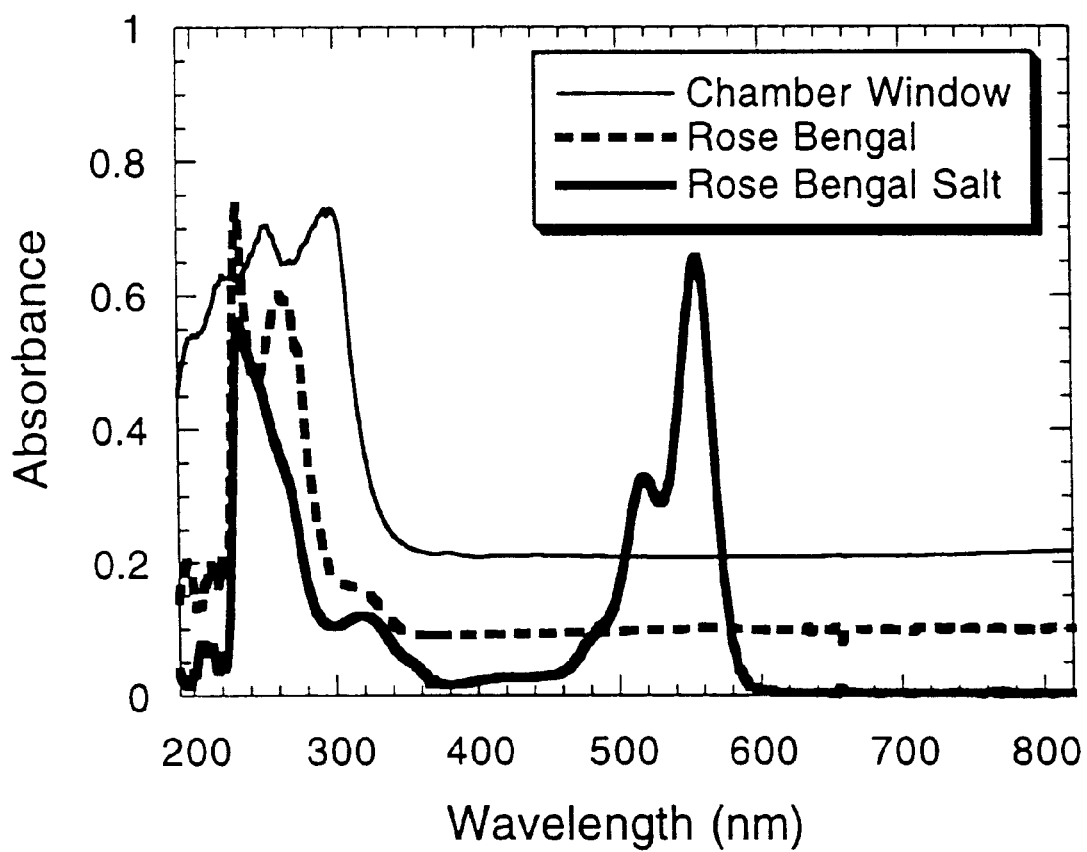
FIG. 3 is a UV-vis spectrum of the chamber window, Rose Bengal ($3.8 \times 10^{-6}$ wt percent) in methylene chloride and Rose Bengal bis(triethylammonium) salt (0.001 wt percent) in methylene chloride.

The photoinitiators used in these experiments were Rose Bengal and Rose Bengal bis(triethyl ammonium) salt obtained from Aldrich, although other initiators may be used. Interestingly, the Rose Bengal and its ammonium salt have dramatically different absorbance spectra in methylene chloride. FIG. 3 shows that the large peak at ~550 nm seen in the Rose Bengal salt is not present in Rose Bengal. Since the chamber window used in these experiments absorbed wavelengths below 350 nm, visible light initiators were used, and the triethyl ammonium Rose Bengal salt, whose absorbance spectrum is shown in FIG. 3 was used in these experiments.

Particle Production.

5–20 wt % methacrylated sebacic anhydride was dissolved in methylene chloride along with 2% photoinitiator by monomer weight. The chamber was pressurized with deoxygenated $CO_2$ by two ISCO compressed gas pumps and allowed to equilibrate to the desired temperature and pressure. The monomer-solvent solution was then pressurized to the desired pressure by a third ISCO pump. The solution was injected into the environment at a constant flow rate (1 ml/min) through the nozzle while the $CO_2$ flowed at a constant rate of 25 mu/min. A high powered light source (1–4 W/cm$^2$) (EFOS, Novacure) with a visible filter (350–650 nm) and a fiber optic liquid light guide was used to initiate the photo-polymerization below the nozzle. A 5 cm Light Line (EFOS) was used to spread out the beam from the light source to give a longer initiating time in the chamber.

After spraying and polymerization, the system was allowed to settle for half an hour before slow depressurization (~30 min) at the operating temperature. This slow depressurization increased the number of particles collected on the scanning electron microscopy (SEM) stub mounted inside the chamber. After depressurization, samples were also taken from both the inside of the chamber and the 0.2 μm filter. The resulting particles were examined using SEM to determine their size and morphology.

The poly (methacrylated sebacic anhydride) (PMSA) particles were also viewed using a fluorescence microscope (data not shown). The Rose Bengal photoinitiator is a fluorescent dye for the microparticles, with an excitation peak at 540 nm and an emission band between 550–600 nm, so the distribution of photoinitiator in the polymerized particles can be visibly characterized.

Figure 4:
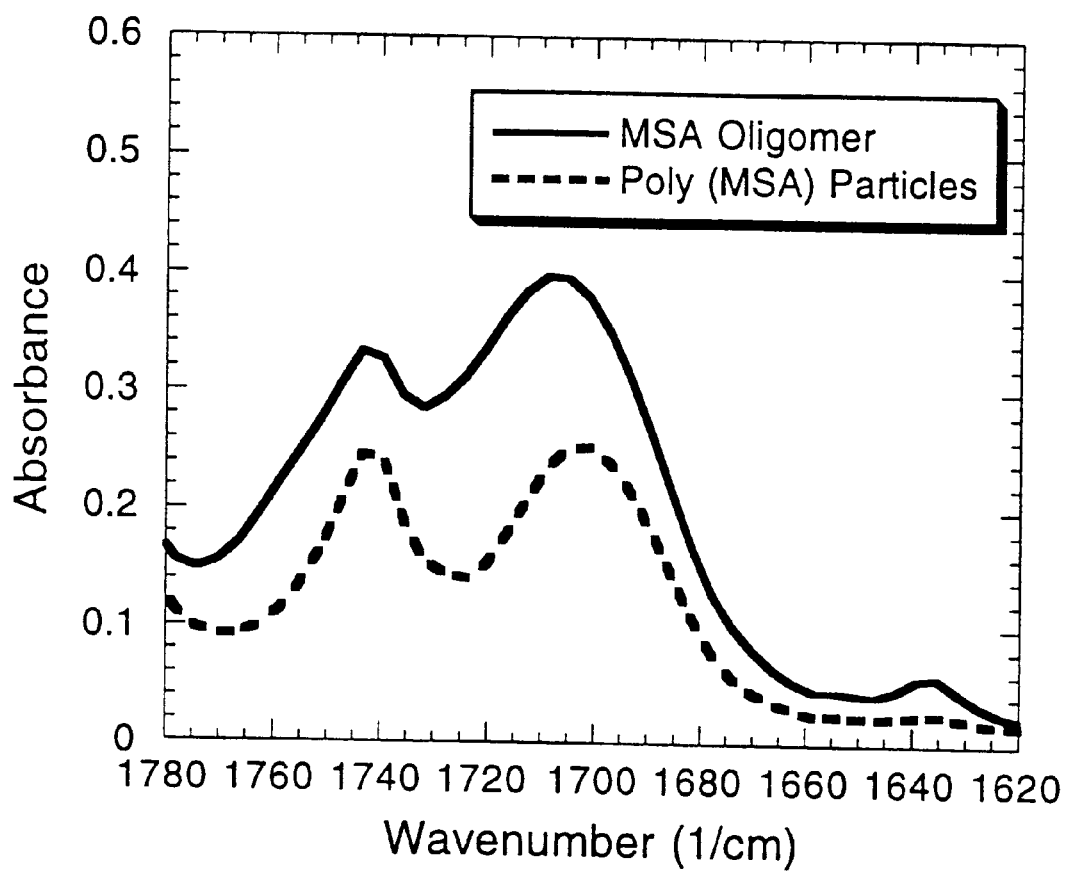
FIG. 4 is a Fourier transform infrared (FTIR) spectra of methacrylated sebacic anhydride oligomer and poly (methacrylated sebacic anhydride).

Polymerization of the multifunctional anhydride monomers during the PCA particle processing was confirmed through Fourier transform infrared (FTIR) spectra of the particles compared to the oligomer (FIG. 4). The peak at 1635 cm$^{-1}$ is assigned to the carbon-carbon double bond stretching in MSA and is largely reduced in relative intensity in the spectrum of (PMSA). The reduction of the peak to immeasurable levels further suggests nearly complete reaction possibly due to added mobility from the solvent.

Figure 5:
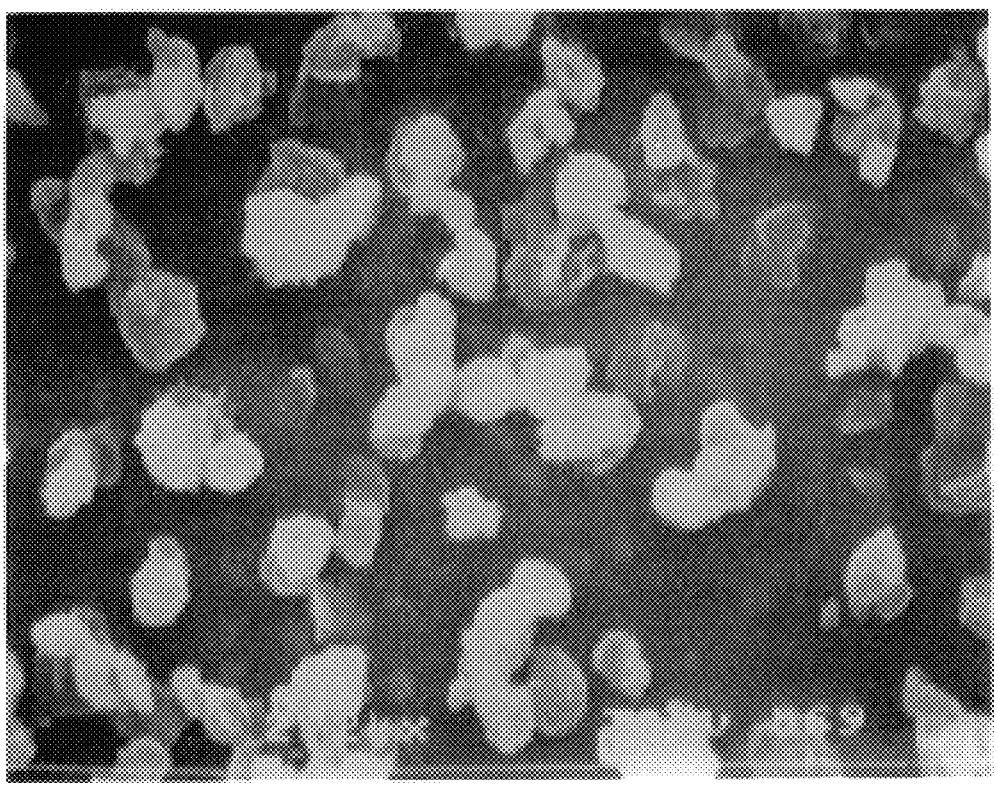
FIG. 5 is a scanning electron microscopy (SEM) photograph of poly(methacrylated sebacic anhydride) microparticles precipitated by spraying and photopolymerizing a 10 wt % MSA solution through a 100 $\mu$m stainless steel capillary nozzle into $CO_2$ at a temperature of 37° C. and pressure of 8.5 MPa.

FIG. 5 is a scanning electron microscopy (SEM) photograph of the poly (methacrylated sebacic anhydride) microparticles magnified 2200 times. These particles were sprayed as described above with a nozzle consisting of a 100 μm stainless steel capillary tube and an operating temperature of 37° C. The particles, although not perfectly spherical, exhibit a round morphology with diameters ranging from 5 to 15 μm. This narrow size distribution is an important advantage of this processing technique since many applications of polymer microparticles require a narrow size distribution, especially biomedical applications where the body may absorb or reject the particles based on their size. The size distribution can also control the release kinetics.

Cloud Point Measurements

Cloud point experiments were performed to measure the solubility of the monomer solution in $CO_2$ at the initial operating conditions of 8.5 MPa and 37° C. A 3 L view cell was injected with a methylene chloride/MSA solution and a pump system insured complete mixing. At a constant temperature of 37° C., the cell was then pressurized with $CO_2$ using a hand pump up to ~95 bar. Next, the cell was slowly depressurized and the pressure at which the monomer solution mixture became visibly insoluble was recorded. The process was repeated three times for each MSA solution concentration and the cloud point pressures were averaged. These results are shown in FIG. 6.

Figure 6:
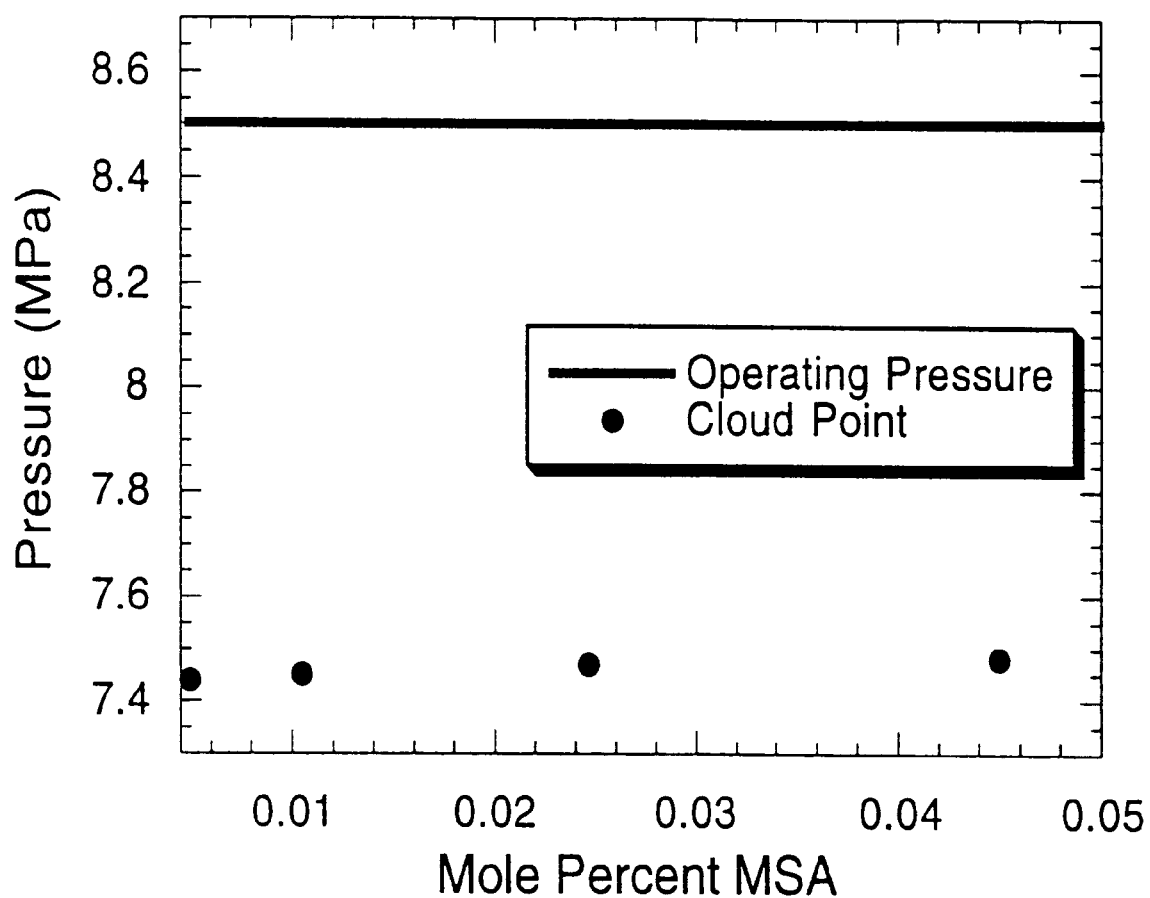
FIG. 6 shows cloud point data for various molar concentrations (consistent with general operating conditions) of MSA monomer in methylene chloride at 37° C.
Figure 7:
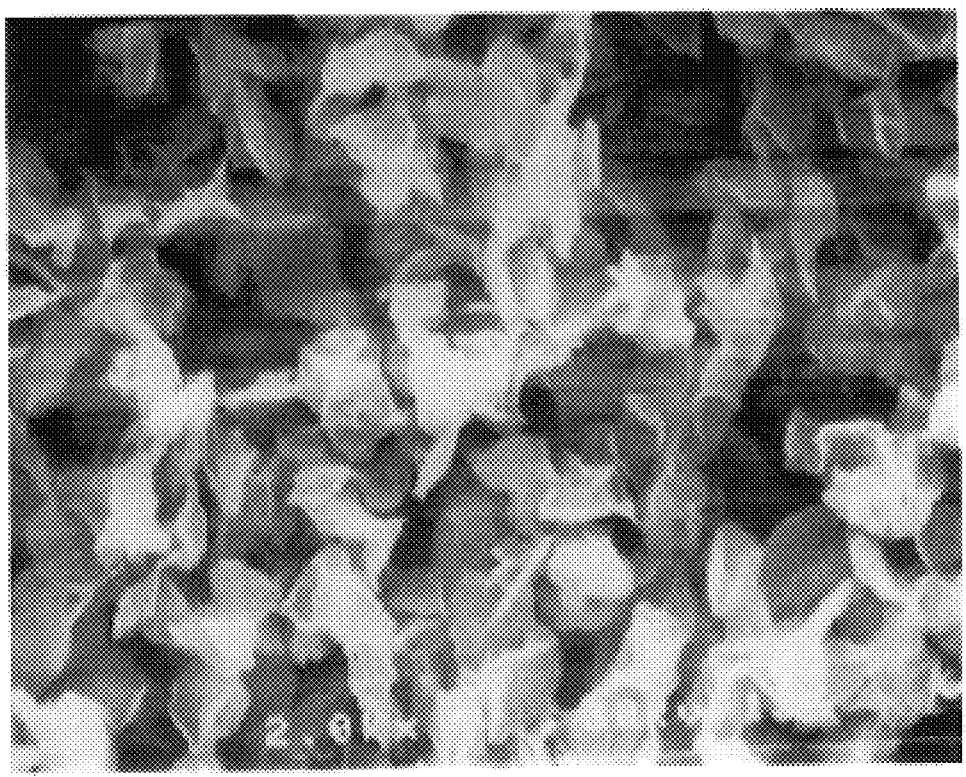
FIG. 7 is an SEM micrograph of PMSA precipitated by spraying and photopolymerizing a 5 wt % MSA solution through an ultrasonic atomizing nozzle into $CO_2$ at a temperature of 25° C. and pressure of 8.5 MPa.
Figure 8A:
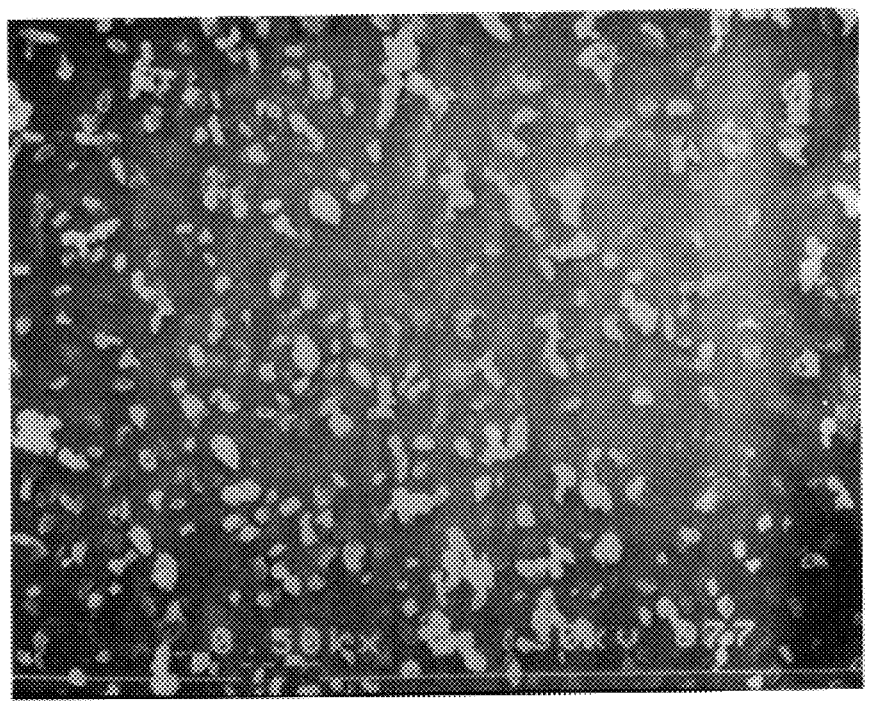
FIG. 8A–8C are SEM micrographs for 5% (A), 10% (B) and 20% (C) MSA.
Figure 8B:
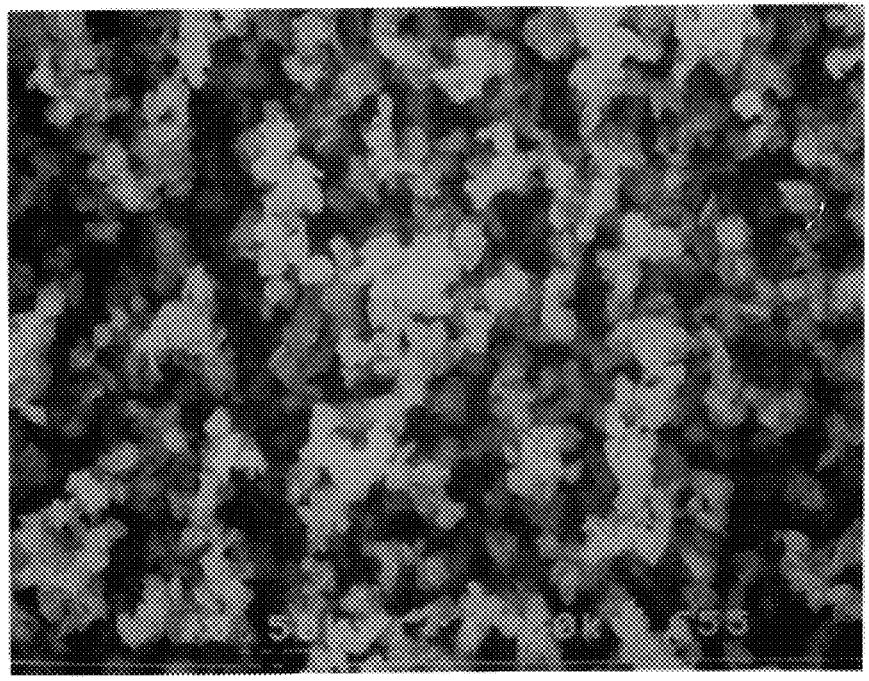
Figure 8C:
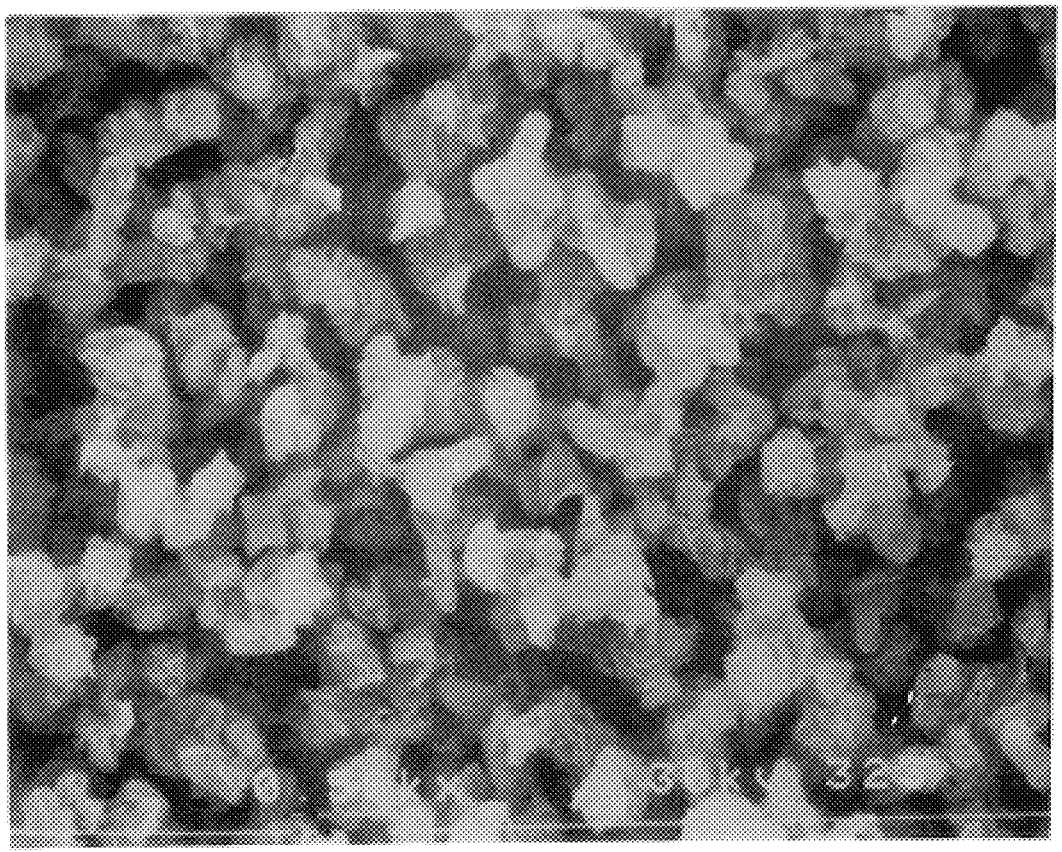
Figure 9A:
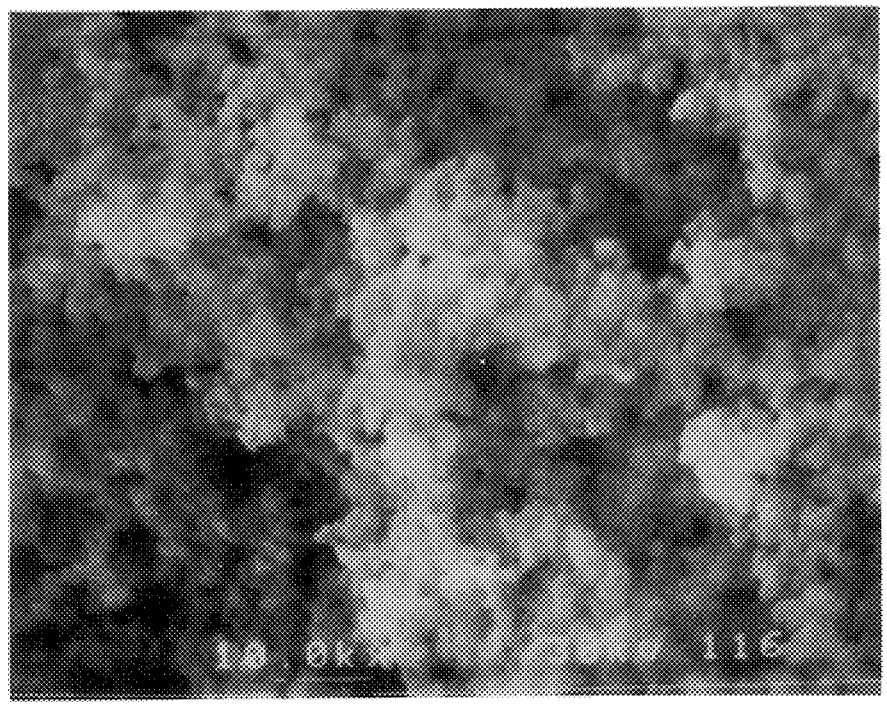
FIG. 9A and 9B are SEM micrographs showing triacrylate polymers under two experimental conditions.
Figure 9B:
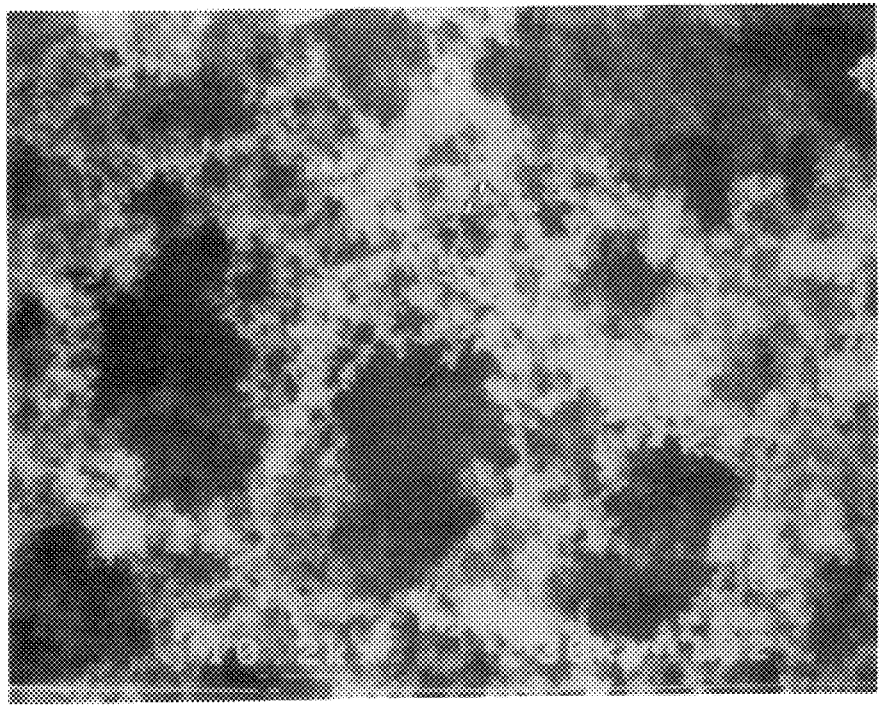
Figure 10A:
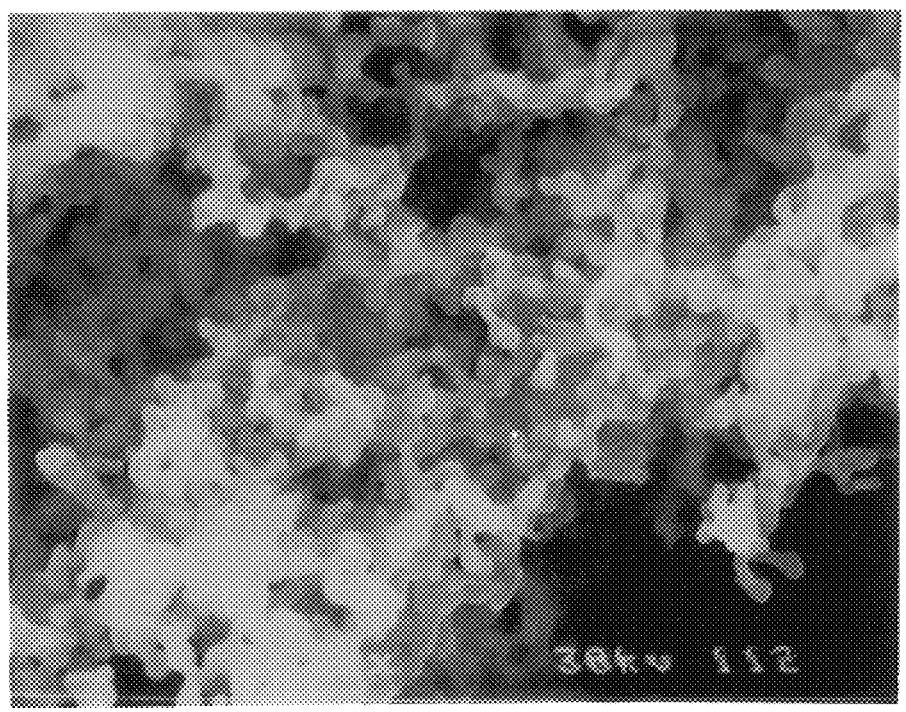
FIG. 10A and 10B are SEM micrographs showing triacrylate polymers under two experimental conditions.
Figure 10B:
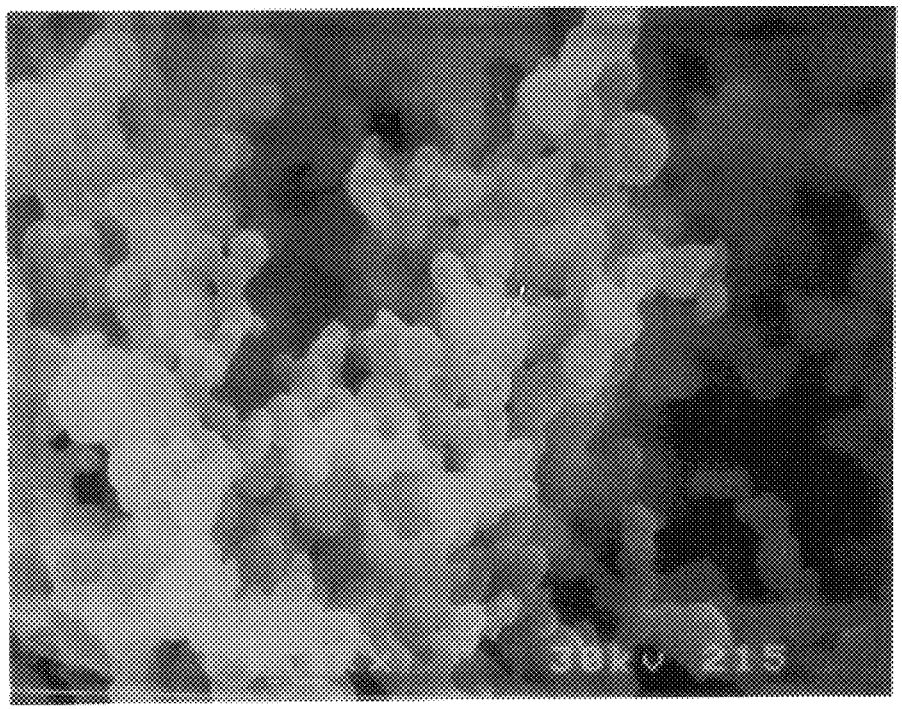
Figure 11:
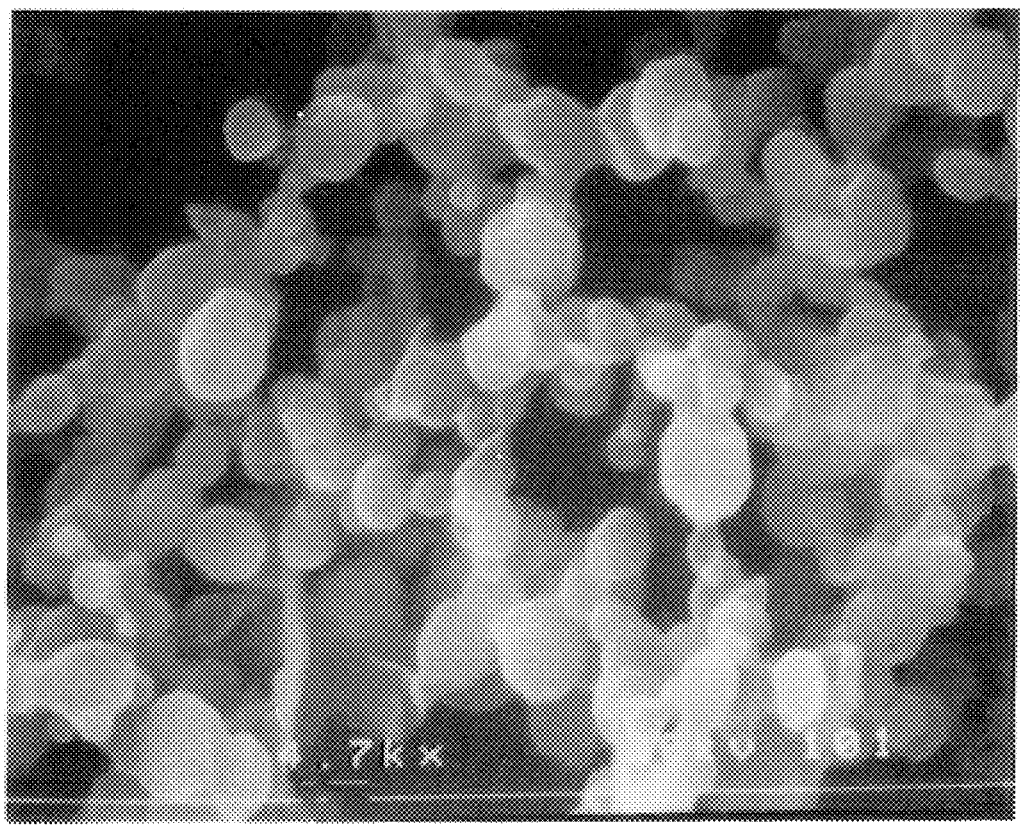
FIG. 11 is a SEM micrograph for 5% MSA/5% PLA copolymer.
Figure 12:
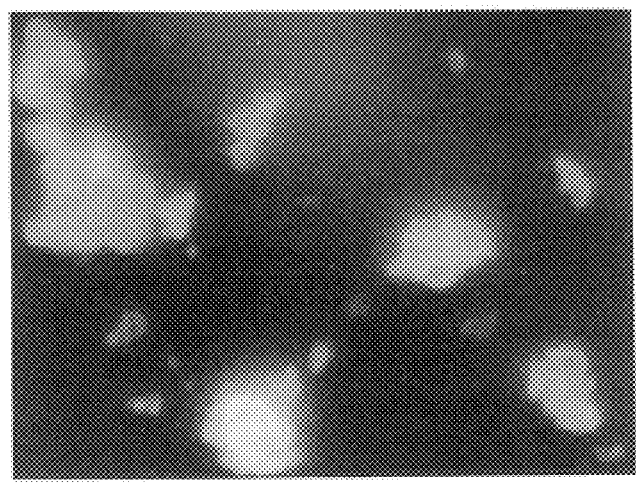
FIG. 12 is a fluorescence micrograph of PMSA particles encapsulated with tacrine.
Figure 13:
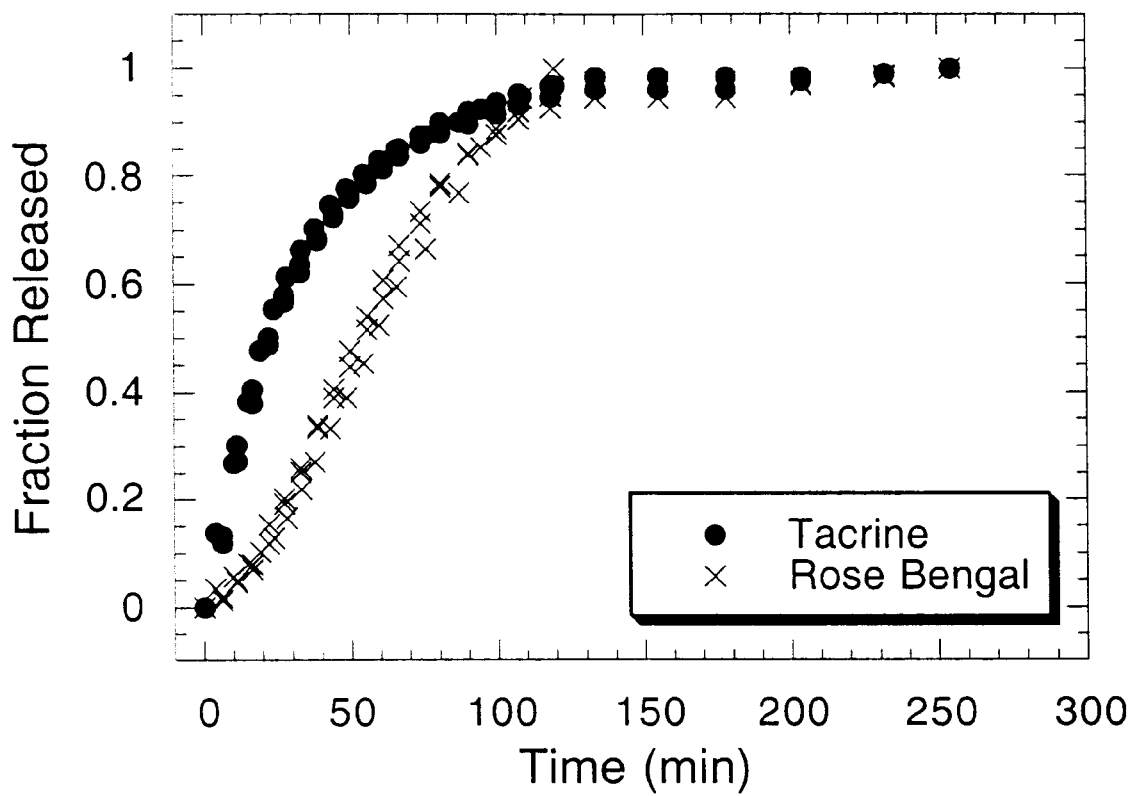
FIG. 13 shows release data from PMSA microparticles encapsulated with tacrine.

FIG. 6 shows the cloud point pressure for this system, which is far below the initial operating pressure implying that the monomer solution is in a gaseous state at the initial operating conditions of 37° C. and 8.5 MPa. If the monomer remains in a gaseous state during photopolymerization, this would significantly dilute the monomer concentration and decrease the rate of polymerization and the probability of microparticle formation during the exposure time. A rapid polymerization rate and a low gel point conversion are desired for this system because the exposure time after atomization is short ($4 \times 10^{-2}$ sec). To circumvent this problem, the operating temperature was lowered to 25° C. such that the operating pressure was constant of PMSA investigated by Muggli et al (Muggli, D. S. et al. (1999) J. Biomed. Mater. Res. 46:271–278). A 5–15 μm particle would degrade in about an hour, according to the calculated kinetic constant, but since oligomerized MSA was used, a longer degradation time should be expected. FIG. 13 shows the release profile of tacrine (absorbance measured at 322 nm (upper data)) and Rose Bengal (absorbance measured at 550 nm (lower data)) from the particles into PBS buffer. The tacrine release profile follows the curve for surface erosion of a sphere as expected. This profile concurs with SEM photographs that show that the particles have a round shape. The shape of the release profile of Rose Bengal indicates there is some influence of diffusion in the release. The Rose Bengal release profile is also affected by photobleaching of particles in room light. This may explain the lag time at the beginning of the Rose Bengal release in FIG. 13.

Release of Particles From an MSA Matrix

Crosslinked particles containing Rose Bengal were incorporated in a MSA matrix and polymerized into disks. Rose Bengal was also homogeneously incorporated into another set of MSA disks and polymerized. Advantages of using a particle-polymer composite include multi-mode degradation and release possible through the use of different biocompatible polymers and drugs, ease of control of surface degradation, and in one particular application, bone growth is facilitated by the resulting porous structures.

Disk samples were 0.25 to 0.3 grams, 13 mm diameter and 1.5 mm thick. Disks were placed in 10 ml of PBS buffer at 37° C. to monitor the degradation.

Figure 14:
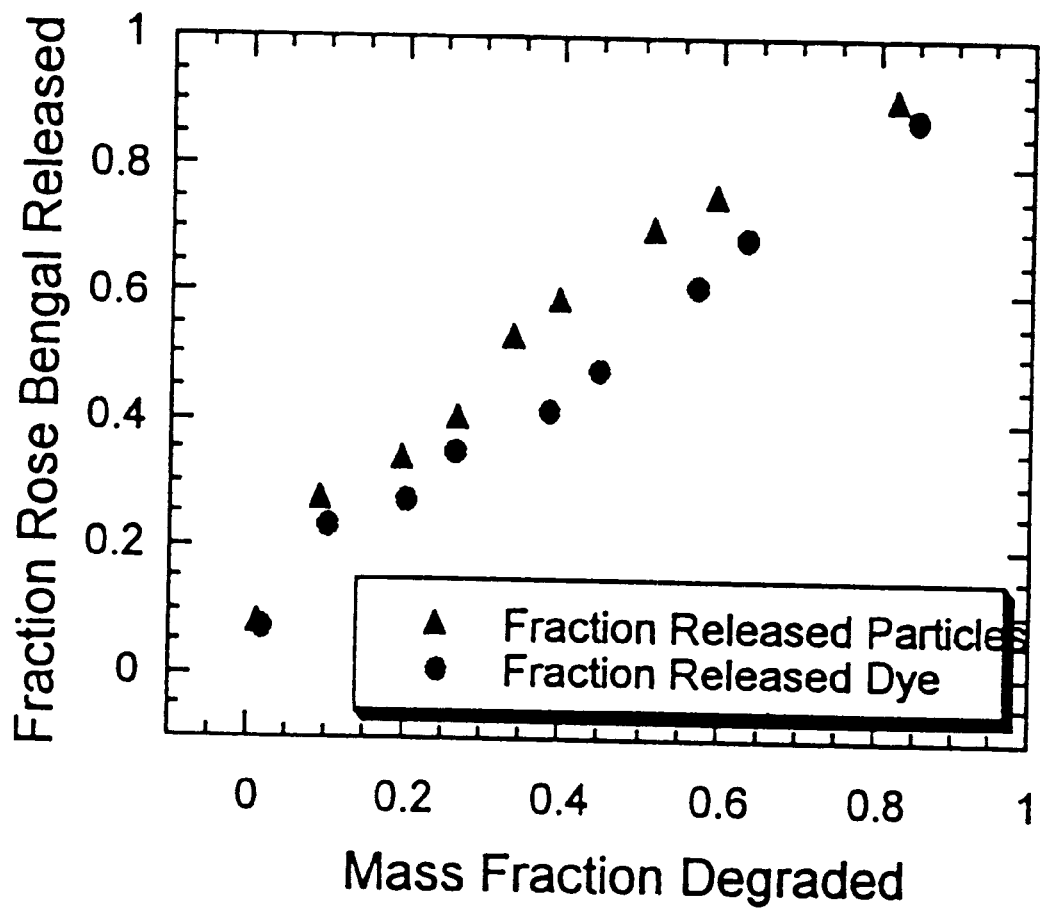
FIG. 14 shows release data from particles containing Rose Bengal incorporated in a MSA matrix and polymerized into disks and release data from Rose Bengal homogeneously incorporated into MSA disks and polymerized.

FIG. 14 shows release behavior for both sets of disks as a function of the mass fraction of the disks that had degraded. The absorbance of Rose Bengal was measured at 550 nm, and the disks were weighed to monitor the degradation. FIG. 14 shows a linear relationship between degradation and release for both homogeneous and heterogeneous disks.

One particular application of the particles is in bone cements. Particles release drugs over time as the bone cement (formed of degradable material) degrades and bone regrows.

Although the description above contains many specificities, these should not be construed as limiting the scope of the invention but as merely providing illustrations of some of the presently preferred embodiments of the invention. For example, antisolvents other than carbon dioxide may be used. Other embodiments and uses are readily apparent to one of ordinary skill in the art without undue experimentation. Thus, the scope of the invention should be determined by the appended claims and their legal equivalents, rather than by the examples given. All references cited herein are hereby incorporated by reference to the extent not inconsistent with the disclosure herewith.

We claim:

1. A method of forming polymer particles comprising:
   exposing a composition comprising at least one polymer precursor, a non-aqueous solvent or solvent mixture, and an antisolvent or antisolvent mixture to photoradiation under conditions whereby particles are formed, wherein the antisolvent solvent is a supercritical or near supercritical fluid in which the polymer precursor is not substantially soluble.

2. The method of claim 1, wherein said polymer precursor is insoluble in said antisolvent or antisolvent mixture and said solvent is soluble in said antisolvent or antisolvent mixture.

3. The method of claim 1, said composition further comprising at least one polymerization initiator.

4. The method of claim 3, wherein said polymerization initiator is selected from the group consisting of initiators activated by light.

5. The method of claim 1, wherein said polymer particles are erodable.

6. The method of claim 5 wherein said composition anther comprises a bioactive substance, whereby polymer particles comprising an erodable polymer and a bioactive substance are formed.

7. The method of claim 1, wherein said polymer particles are nonerodable.

8. The method of claim 1, wherein said polymer particles are biodegradable.

9. The method of claim 1, wherein said polymer particles are nonbiodegradable.

10. The method of claim 1, wherein said polymer particles are biocompatible.

11. The method of claim 1, said composition further comprising a bioactive material whereby polymer particles which also comprise a bioactive material are formed.

12. A pharmaceutical composition comprising polymer particles produced by the method of claim 1 and a pharmaceutically acceptable carrier.

13. The method of claim 1, wherein said composition is passed through a nozzle.

14. The method of claim 1, wherein said polymer precursor is photosensitive.

15. The method of claim 1, wherein said polymer particles produced are between about $0.001\mu$ to about 100 μm in diameter.

16. The method of claim 1, wherein said polymer particles produced are between about 2 to about 20 μm in diameter.

17. The method of claim 1, wherein said polymer precursor is selected from the group consisting of radically polymerizable precursors.

18. The method of claim 1, wherein said polymer precursor is selected from the group consisting of tonically polymerizable precursors.

19. The method of claim 1, wherein said solvent is selected from the group consisting of non-aqueous solvents and mixtures thereof.

20. The method of claim 19, wherein said solvent is selected from the group consisting of methylene chloride, methanol, toluene, propanol, ethanol, acetone, ethers, hexanes, heptane, and mixtures thereof.

21. The method of claim 1, wherein said polymer precursor is methacrylated sebacic anhydride and said solvent is methylene chloride and said antisolvent is carbon dioxide.

22. The method of claim 1, wherein said antisolvent is selected from the group consisting of: carbon dioxide, nitrogen, ethane and propane.

23. The method of claim 1, wherein the polymers of said polymer particles are linear.

24. The method of claim 1, wherein said polymer particles are crosslinked.

25. The method of claim 1, further comprising the step of collecting said polymer particles, wherein said polymer particles are substantially free of solvent.

26. A method of forming polymer particles comprising:
   (a) contacting a solution comprising a non-aqueous solvent or solvent mixture and at least one polymer precursor with an antisolvent or antisolvent mixture under conditions whereby particles are generated, wherein the antisolvent is a supercritical or near supercritical fluid in which the polymer precursor is not substantially soluble;
   (b) exposing said particles to photoradiation whereby polymer particles are formed.

27. The method of claim 26, wherein said solvent or solvent mixture is soluble in said antisolvent or antisolvent mixture and said polymer precursor is insoluble in said antisolvent or antisolvent mixture under conditions whereby particles are generated.

28. The method of claim 26, wherein said polymer precursor is dissolved in said solvent or solvent mixture to form said solution; and wherein said solution is contacted with an antisolvent or antisolvent mixture in which said polymer precursor is insoluble.

29. The method of claim 26, wherein said solution also comprises at least one polymerization initiator.

30. The method of claim 26, wherein said antisolvent or antisolvent mixture is in an optically accessible chamber.

31. A method of forming copolymers comprising:
  (a) dissolving or suspending at least two polymer precursors or at least one polymer precursor and at least one polymer in a non-aqueous solvent or solvent mixture to form a solution;
  (b) contacting said solution with an antisolvent or antisolvent mixture to form a composition;
  (c) exposing said composition to photoradiation wherein said solvent or solvent mixture is soluble in said antisolvent or antisolvent mixture.

32. A method of forming copolymers comprising:
  (a) dissolving or suspending least one polymer precursor or at least one polymer in a non-aqueous solvent or solvent mixture to form a solution;
  (b) contacting said solution with an antisolvent or antisolvent mixture containing at least one polymer precursor or at least one polymer to form a composition;
  (c) exposing said composition to photoradiation provided that at least one polymer precursor is used, wherein said solvent or solvent mixture is soluble in said antisolvent or antisolvent mixture.

33. A method for controlled release of a desired substance using polymer particles comprising:
  (a) preparing polymer particles that comprise a degradable polymer and a desired substance by exposing a composition comprising at least one polymer precursor, the desired substance and an antisolvent or antisolvent mixture to photoradiation under conditions whereby particles are formed;
  (b) exposing said polymer particles to conditions under which the polymer is degraded.

34. The method of claim 33, wherein the polymer particles are prepared by the method of claim 1.

35. The method of claim 33 wherein the desired substance is a bioactive material.

36. The method of claim 33 wherein the desired substance is a fertilizer.

37. The method of claim 33 wherein the desired substance is a pesticide.

38. The method of claim 33 wherein the desired substance is a fragrance.

39. The method of claim 33 wherein the desired substance is a corrosion inhibitor.

40. A method of forming polymer particles comprising: exposing a composition comprising at least one liquid polymer and a non-aqueous antisolvent or antisolvent mixture to photoradiation under conditions whereby polymer particles are formed.

41. The method of claim 40 wherein said polymer precursor is insoluble in said antisolvent or antisolvent mixture.

42. The method of claim 40, wherein said polymer precursor is selected from the group consisting of radically polymerizable polymer precursors.

43. A method for controlled release of a desired substance using polymer particles comprising:
  a) preparing polymer particles that comprise a biodegradable polymer and a desired substance by exposing a composition comprising at least one polymer precursor, the desired substance and an antisolvent or antisolvent mixture to photoradiation under conditions whereby particles are formed;
  b) exposing said polymer particles to a biological system.

44. The method of claim 43 wherein the desired substance is a bioactive material.

* * * * *